US007531322B2

(12) United States Patent
Cichutek et al.

(10) Patent No.: US 7,531,322 B2
(45) Date of Patent: May 12, 2009

(54) CELL-SPECIFIC RETROVIRAL VECTORS WITH ANTIBODY DOMAINS AND METHOD FOR THE PRODUCTION THEREOF FOR SELECTIVE GENE TRANSFER

(75) Inventors: Klaus Cichutek, Langen (DE); Martin Engelstadter, Roedermark (DE)

(73) Assignee: Bundesrepublik Deutschland, Langen (DE)

( * ) Notice: Subject to any disclaimer, the term of this patent is extended or adjusted under 35 U.S.C. 154(b) by 272 days.

(21) Appl. No.: 11/108,045

(22) Filed: Apr. 15, 2005

(65) Prior Publication Data

US 2005/0191740 A1 Sep. 1, 2005

Related U.S. Application Data

(63) Continuation of application No. 09/555,350, filed as application No. PCT/DE98/03543 on Nov. 27, 1998, now abandoned.

(30) Foreign Application Priority Data

Nov. 28, 1997 (DE) ................................ 197 25 854

(51) Int. Cl.
*C12P 21/00* (2006.01)
*C12N 15/00* (2006.01)
(52) U.S. Cl. .................................... 435/69.1; 435/320.1
(58) Field of Classification Search ....................... None
See application file for complete search history.

(56) References Cited

U.S. PATENT DOCUMENTS

| 5,869,331 | A | 2/1999 | Dornburg |
| 6,352,694 | B1 | 3/2002 | June |

FOREIGN PATENT DOCUMENTS

| WO | WO 95/23846 | 8/1995 |
| WO | WO 96/30504 | 3/1996 |

OTHER PUBLICATIONS

Anderson, "Human Gene Therapy" *Science* 256:808-813, 1992.
Buchschacher et al., "Human Immunodeficiency Virus Vectors for Inducible Expression of Foreign Genes" *J. Virol.*, 66:2731-2739, 1992.
Burns et al., "Vesicular stomatitis virus G glycoprotein pseudotyped retroviral vectors: Concentration to very high titer and efficient gene transfer into mammalian and nonmammalian cells" *Proc. Natl. Acad. Sci USA*, 90:8033-8037, 1993.
Chu et al., "Toward Highly Efficient Cell-Type-Specific Gene Transfer with Retroviral Vectors Displaying Single-chain Antibodies" *J. Virol.* 71:720-725, 1997.
Cosset et al., "Retroviral Retargeting by Envelopes Expressing an N-Terminal Binding Domain" *J. Virol.*, 69:6314-6322, 1995.
Huston et al., "Protein Engineering of single-chain Fv Analogs and Fusion Proteins" *Methods Enzymol.*, 203:46-88, 1991.
Kasahara et al., "Tissue-Specific Targeting of Retroviral Vectors Through Ligand-Receptor Interactions" *Science*, 266:1373-1375, 1994.
Mammano et al., "Truncation of the Human Immunodeficiency Virus Type 1 Envelope Glycoprotein Allows Efficient Pseudotyping of Moloney Murine Leukemia Virus Particles and Gene Transfer into $CD4^+$Cells" *J. Virol*, 71:3341-3345, 1997.
Morgan et al., "Analysis of the Functional and Host Range-Determining Regions of the Murine Ecotropic and Amphotropic Retrovirus Envelope Proteins" *J. Virol.*, 67:4712-4721, 1993.
Naldini et al., "In Vivo Gene Delivery and Stable Transduction of Nondividiing Cells by a Lentiviral Vector" *Science*, 272:263-267, 1996.
Poeschla et al., "Development of HIV vectors for anti-HIV gene therapy" *Proc. Natl. Acad. Sci USA*, 93:11395-11399, 1996.
Porter et al., "Comparison of Efficiency of Infection of Human Gene Therapy Target Cells via Four Different Retroviral Receptors" *Hum Gene Ther*. 7:913-919, 1996.
Reiser et al., "Transduction of nondividing cells using pseudotyped defective high-titer HIV type 1 particles" *Proc. Natl. Acad. Sci. USA*, 93:15266-15271, 1996.
Russel et al., "Retroviral vectors displaying functional antibody fragments" *Nucl. Acids Res.* 21:1081-1085, 1993.
Schnierle et al., "Pseudotyping of murine leukemia virus with the envelope glycoproteins of HIV generates a retroviral vector with specificity of infection for CD4-expressing cells" *Proc. Natl. Acad. Sci. USA*, 94:8640-8645, 1997.
Somia et al., "Generation of targeted retroviral vectors by using single-chain variable fragment: An approach to in vivo gene delivery" *Proc. Natl. Acad. Sci. USA*, 92:7570-7574, 1995.
Takeuschi et al., "Type C Retrovirus Inactivation by Human complement Is Determined by both the Viral Genome and the Producer Cell" *J. Virol.*, 68:8001-8007, 1994.
Takeuschi et al., "Retroviral Pseudotypes Produced by Rescue of a Moloney Murine Leukemia Virus Vector by C-type, but Not D-type, Retroviruses" *Virology*, 186:792-794, 1992.
Valsesia-Wittmann et al., "Improvement of Retroviral Retargeting by Using Amino Acid Spacers between an Additional Binding Domain and the N Terminus of Moloney Murine Leukemia Virus SU" *J. Virol.*, 70:2059-2064, 1996.
Vile et al., "A Murine Cell Line Producing HTLV-I Pseudotype Virions Carrying a Selectable Marker Gene" *Virology* 186:420-424, 1991.
Chaudhary et al., *Proc. Natl. Acad. Sci USA* 87:1066, 1990.
Chiswell et al., *TIBTECH* 10:80, 1992.
Chu et al., *J. Virol.* 69:2659-2663, 1995.
Chu et al., *Gene Therapy* 1:292-299, 1994.
Chu et al., *BioTechniques* 18:890-899, 1995.

(Continued)

*Primary Examiner*—Stacy B Chen
(74) *Attorney, Agent, or Firm*—Fish & Richardson P.C.

(57) ABSTRACT

The invention relates to cell-specific retroviral vectors with antibody recognition domains (scFv), which are suitable for cell-specific transduction of a selected mammal cell type (cell targeting), to methods for the production of the cell-specific retroviral vectors and to the use thereof in gene transfers into selected cells. The invention further relates to retroviral packaging cells to obtain cell-specific vectors according to the present invention.

12 Claims, 9 Drawing Sheets

OTHER PUBLICATIONS

Figure 1:
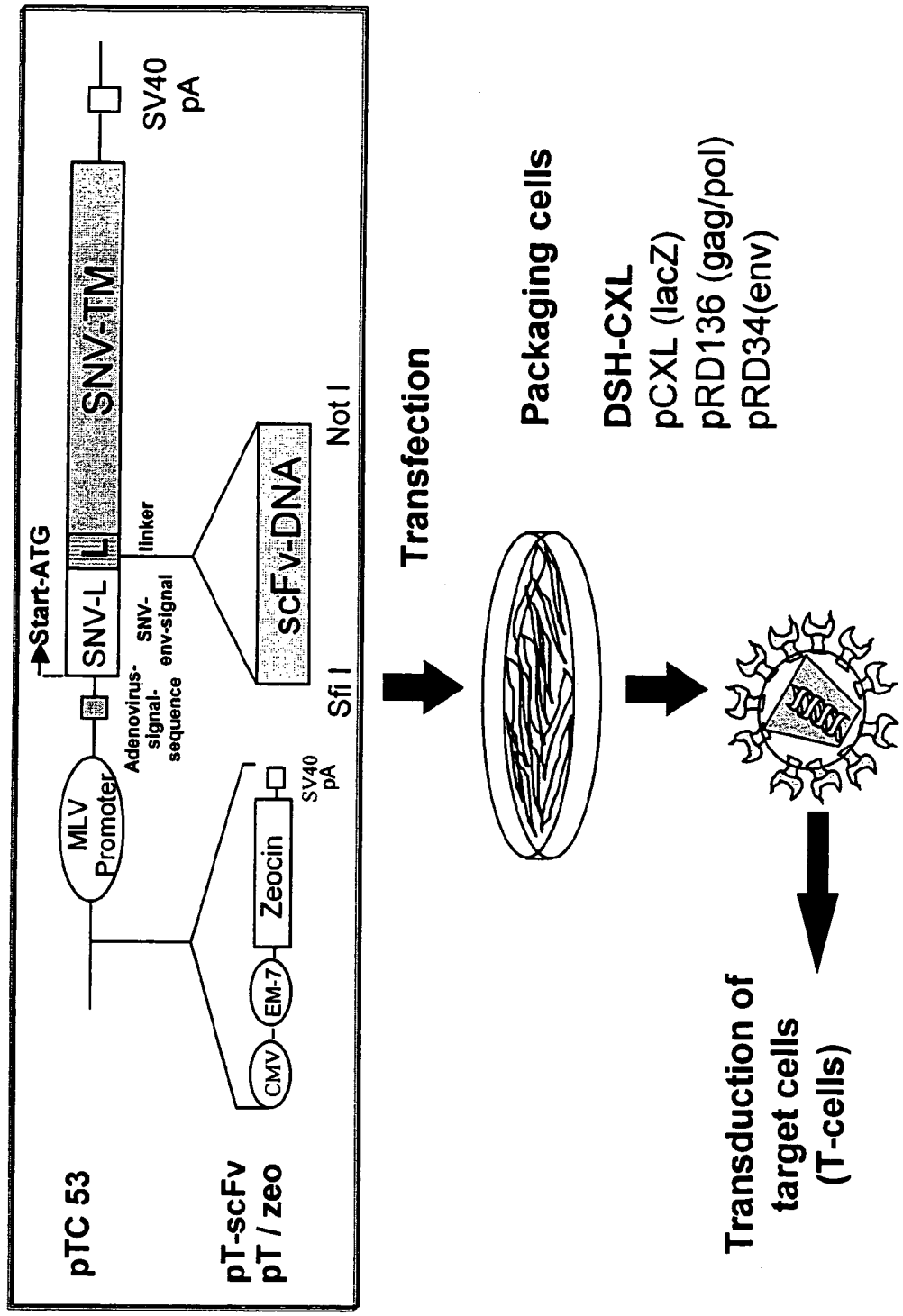
Figure 2:
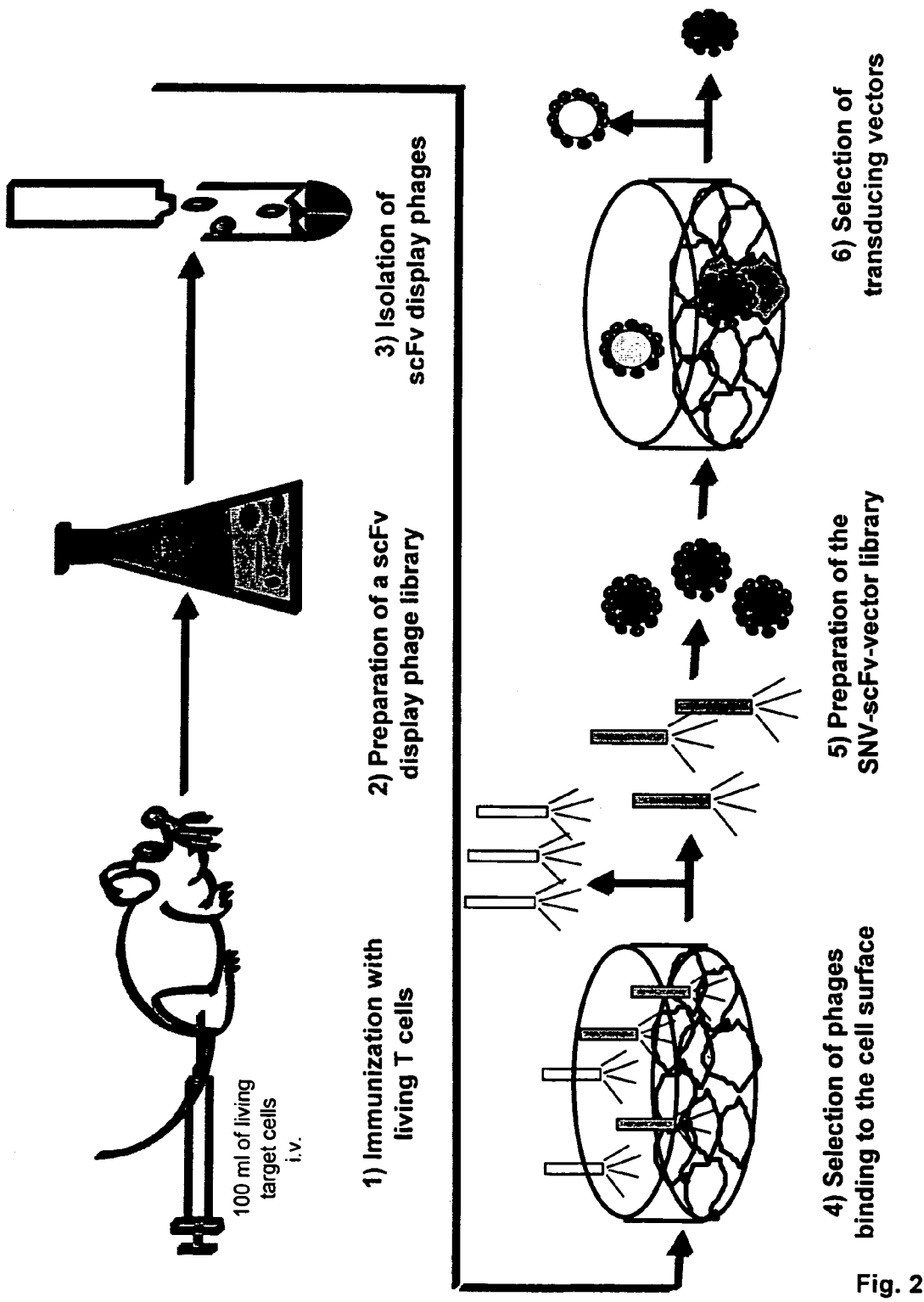
Figure 3:
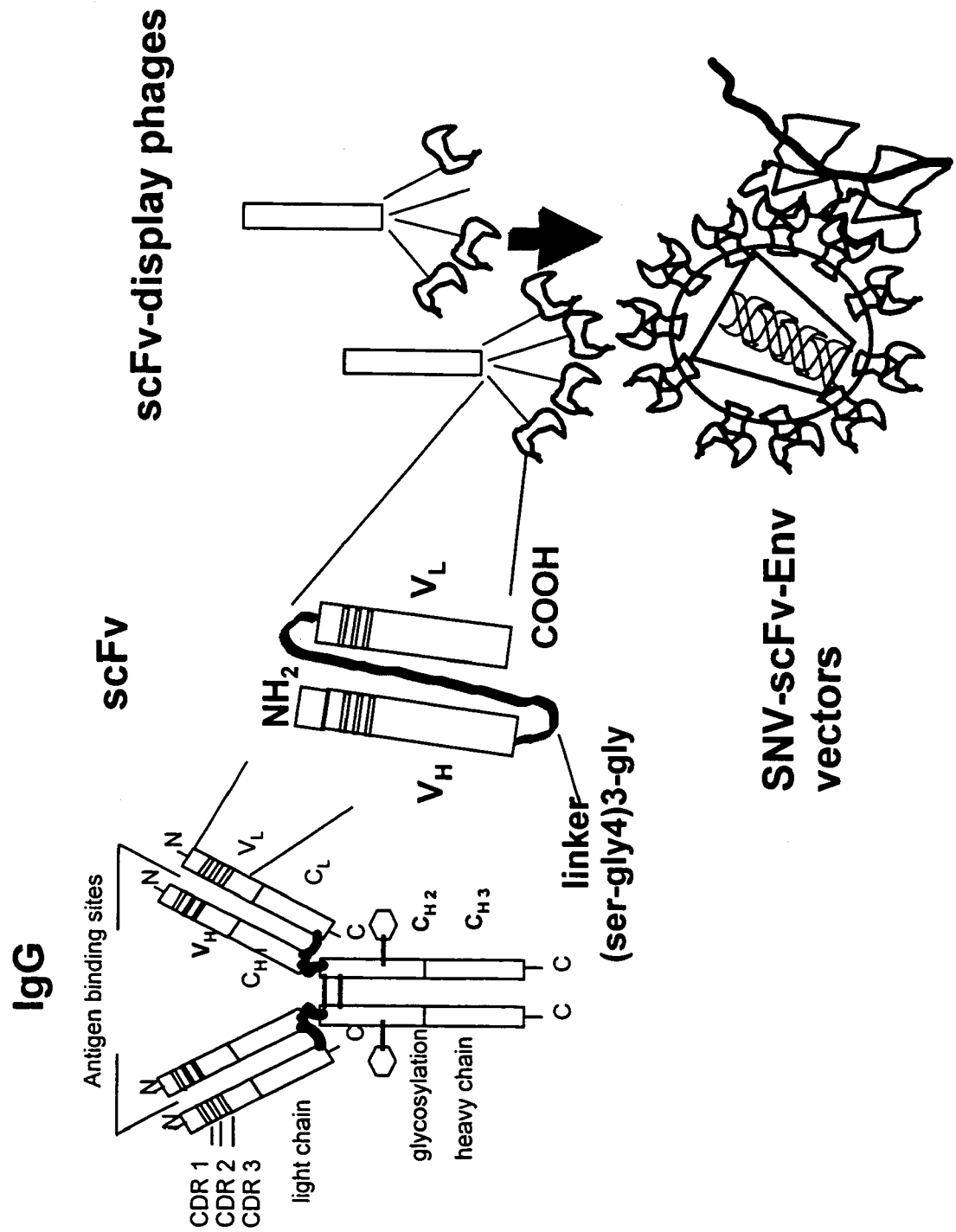

Clackson et al., *Nature* 352:624, 1991.
Clapham et al., *Virol.* 158:44-51, 1987.
Dornburg, *Gene Therapy* 2:1-10, 1995.
Huston et al., *Methods Enzymol.* 203:46-88, 1991.
Huston et al., "[3] Protein Engineering of Single-Chain Fv Analogs and Fusion Proteins" *Methods in Enzymology* 203:46-89, 1991.
Kassahara et al., "Tissue-Specific Targeting of Retroviral Vectors Through Ligand-Receptor Interactions" *Science* 266:1373-1376, 1994.
Marks et al., *J. Mol. Biol.* 222:581, 1991.
Marks et al., *BioTechnology* 10:779, 1992.
Martinez et al., *Virol.* 208:234-241, 1995.
McCafferty et al., *Nature* 348:552, 1990.
Russel et al., *Nucl. Acids Res.* 21:1081-1085, 1993.
Sheay et al., *BioTechniques* 15:856-861, 1993.
Schnierle et al., Pseudotyping of murine leukemia virus with the envelope glycoproteins of HIV generates a retroviral vector with specificity of infection for CD4-expressing cells *Proc. Natl. Acad. Sci. USA* 94:8640-8645, 1997.
Valseasia-Wittmann et al., "Improvement of Retroviral Retargeting by Using Amino Acid Spacers between an Additional Binding Domain and the N Terminus of Moloney Murine Leukemia Virus SU" *J. Virol.* 70:2059-2064, 1996.
Colcher et al., *J. Natl. Cancer Inst.* 82:1191-1197, 1990.
Novotny et al., "Immunology", in *Molecular Biology and Biotechnology: A Comprehensive Desk Reference*; Ed. R.A. Meyers (1995) VCH Publishers Inc.; pp. 449-458.

Fig. 4 (page 1 of 6)

Fig. 4 (page 2 of 6)

```
1655 CTC GGC CCG TGC ATT ATG AAG ACC CTG ACT CCC ATT ATA CAT GAC AAA ATT CAG GCA GTA AAA TCC TAG CACTAGTC 1731
 211 L   G   P   C   I   M   K   T   L   T   R   I   I   H   D   K   I   Q   A   V   K   S   *            233

1732 CCACAGTACAAGCCACTCCAACACAG ATG GAT ACC CTA GGG GTC CGA TGG GTC TGA GTC TAA GATCGATCGAAT                 1815
                                M   D   T   L   G   V   R   W   V   *                                      15
                                1

1816 TCCTAGTCA ATG ATT TGA CCAGA ATG TAC AAG AGC AGT GGG GAA TGT GGG AGG GGC TTA CGA AGG CCT TAA GTGACTA   1894
            M   I   *        M   Y   K   S   S   G   E   C   G   R   G   L   R   R   P   *              16
            1                 1

1895 GGTACCGGATCCAGAC ATG ATA AGA TAC ATT GAT GAG TTT GGA CAA ACC ACA ACT AGA ATG CAG TGA AAAAA ATG CTT    1972
                     M   I   R   Y   I   D   E   F   G   Q   T   T   T   R   M   Q   *              M   L  2
                     1                                                                               1

1973 TAT TTG TGA AATTGTG ATG CTA TTG CTT TAT TTG TAA CCATTATAAGTGCTATAAACAGTAACAACAATGATTGATTGATTTTGATTT  2060
  3  Y   L   *          M   L   L   L   Y   L   *                                                          7
                        1

2061 ATG TTT CAG GTT CAG GGG GAG GTC TGG GAG GTT TTT TAA AGCAAGTAAAACCTTACAATCAAGCTGGGCAAGCTAGATCTAGCTT   2147
 1 M   F   Q   V   Q   G   E   V   W   E   E   V   F   *                                                 11

2148 GCGTAATC ATG GTC ATA GCT GTT TCC TGT GTG AAA TTG TTA TCC GCT CAC AAT TCC ACA CAA CAT ACG AGC CGG    2222
         M   V   I   A   V   S   C   V   K   L   L   S   A   H   N   S   T   Q   H   T   S   R        22
         1

2223 AAG CAT AAA GTG TAA AGCCTGGGGTCCTA ATG ACT GAG CTA ACT CAC ATT AAT TGC GTT GCG CTC ACT GCC CCG TTT 2300
  23 K   H   K   V   *                  M   S   E   L   T   H   I   N   C   V   A   L   T   A   R   F  16
                                         1
```

Fig. 4 (page 3 of 6)

Fig. 4 (page 4 of 6)

Fig. 4 (page 5 of 6)

```
4122 AGGAAGGCAAA ATG CCG CAA AAA AGG GAA TAA GGGGACACGGA ATG TTG AAT ACT CAT ACT CTT CCT TTT TCA ATA   4199
   1              M   P   Q   K   R   E   *              M   L   N   T   H   T   L   P   F   S   I    11

4200 TTA TTG AAG CAT TTG TCA GGG TTA TTG TCT CAT GAG CGG ATA CAT CAT ATT TGA ATG TAT TTA GAA AAA TAA ACAAATA   4275
  12  L   L   K   H   L   S   G   L   L   S   H   E   R   I   H   H   I   *   M   Y   L   E   K   *            6

4276 GGGTTCCGGACATTCCGGAAAGTCCACTGACGTCTAAGAAACCATTATATC ATG ACA TTA ACC TAT AAA AAT AGG CGT ATC   4365
   1                                                    M   T   L   T   Y   K   N   R   R   I         10

4366 ACG AGG CCC TTT CTC CCG CCT TTC GGT GAT GAC GGT GAA AAC CTC TGA CAC ATG CAG CCG GAG ACG GTC   4440
  11  T   R   P   F   L   R   P   F   G   D   D   G   E   N   L   *   H   M   Q   L   P   E   T   V    7

4441 ACA GCT TGT CTG TAA GGGG ATG CCG GGA GCA GAC AAG CCC GTC AGG CGG GTG TTG GCG CGT GTC CGG   4516
   8  T   A   C   L   *       M   P   G   A   D   K   P   V   R   R   V   L   A   G   V   G       19

4517 GCT GGC TTA ACT ATG CGG CAT CAG AGC AGA TTG TAC TGA GAGTCACCAT ATG CGG TGT GAA ATA CCG CAC AGA TGC   4593
  20  A   G   L   T   M   R   H   Q   S   R   R   L   Y   *              M   R   C   E   I   P   H   R   C    9

4594 GTA AGG AGA AAA TAC CGC ATC AGG CTG CAT TCG CCA TTC AGG CTG CCG AAC TGT TGG GAA GGG CGA TTG GTG CGG   4668
  10  V   R   R   K   Y   R   I   R   L   H   S   P   F   R   L   R   N   C   W   E   G   R   S   V   R     34

4669 GCC TCT TCG CTA TTA CGC CAG CTG CGA AAA CGG GGA TGT GCA AGG CGA TTA AGT TGG GTA ACG CCA GGG TTT   4743
  35  A   S   S   L   L   R   Q   L   R   K   R   G   C   A   R   R   L   S   W   V   T   P   G   F     59

4744 TCC CAG TCA CGA CGT TGT AAA ACG ACG GCC AGT   4776
  60  S   Q   S   R   R   C   K   T   T   A   S    70
```

Fig. 4 (page 6 of 6)

SEQUENCE LISTING

<160> NUMBER OF SEQ ID NOS: 35

<210> SEQ ID NO 1
<211> LENGTH: 4776
<212> TYPE: DNA
<213> ORGANISM: Artificial Sequence
<220> FEATURE:
<223> OTHER INFORMATION: Synthetically generated DNA

<400> SEQUENCE: 1

```
gaattcccgt acgagccata gataaaataa aagattttat ttagtctcca gaaaaagggg      60
ggaatgaaag accccacctg taggtttggc aagctagctt aagtaacgcc attttgcaag     120
gcatggaaaa atacataact gagaatagag aagttcagat caaggtcagg aacagatgga     180
acagctgaat atgggccaaa caggatatct gtggtaagca gttcctgccc cggctcaggg     240
ccaagaacag atggaacagc tgaatatggg ccaaacagga tatctgtggt aagcagttcc     300
tgccccggct cagggccaag aacagatggt ccccagatgc ggtccagccc tcagcagttt     360
ctagagaacc atcagatgtt tccagggtgc cccaaggacc tgaaatgacc ctgtgcctta     420
tttgaactaa ccaatcagtt cgcttctcgc ttctgttcgc gcgcttctgc tccccgagct     480
caataaaaga gcccacaacc cctcactcgg ggcgccagtc ctccgattga ctgagtcgcc     540
cgggtggggg agctcgctgt tgggctcgcg gttgaggaca aactcttcgc ggtctttcca     600
gtactcttgg atcggaaacc cgtcggcctc cgaacggtac tccgccaccg agggacctga     660
gcgagtccgc atcgaccgga tcggaaaacc tctcgagaaa ggcgtctaac cagtcacagt     720
```

-continued

```
cgcaaggtag gctgagcacc gtggccgggc ggcacgggtg gcggtcgggg ttgtttctgg      780
cggaggtgct gctgatgatg taattaagta ggcggtcttg agacggcgat ggtcgaggtg      840
aggtgtggca ggcttgagat ctggccatac acttgagtga caatgacatc cactttgcct      900
ttctctccac aggtgtccac tcccaggtcc aaccggatcc gagctccacc gcggtaaagg      960
tcgctgggaa gaccccgtgg atccaccact ctcgactcaa gaaagctcct gacaaccaag     1020
aagaatggac tgtctcacca acctccgatc cgctgagggt aaagttgacc aggcgagcaa     1080
aatcctaatt ctccttgtgg cttggtgggg gtttgggacc actgccgaag tttcgactgc     1140
cggctccggg ggcggtggtt ctggtggtgg ttctggtggt ggtggttctg gtggtggtgg     1200
ttctggcgcc agcccagtcc agtttatccc cctgcttgtg ggtctaggga tttcaggggc     1260
tacacttgct ggtggaacgg ggcttggggt ctccgttcac acttatcaca agctctctaa     1320
tcaattgatt gaagatgtcc aggctctttc agggaccatc aatgacctac aggaccagat     1380
tgactccctg gctgaggttg tcttacaaaa tagaagaggg ttagacctat tgactgccga     1440
acaaggagga atatgtctcg cactccagga gaagtgttgt ttttacgcta acaagtcggg     1500
tatcgtacgt gacaagatcc gaaaactcca agaggacctt atcgagagaa aacgtgcact     1560
gtacgacaac cccctgtgga gcggcttgaa cggcttcctt ccatatttgc taccccttgtt     1620
aggcccccctg tttgggctca tattgttcct gaccctcggc ccgtgcatta tgaagaccct     1680
gactcgcatt atacatgaca aaattcaggc agtaaaatcc tagcactagt cccacagtac     1740
aagccactcc aacagagat ggatacccta ggggtccgat ggtctaagaa ttctcgagtc     1800
taagatcgat cgaattccta ggtcaatgat tgaccagaa tgtacaagag cagtggggaa     1860
tgtgggaggg gcttacgaag gccttaagtg actaggtacc cgatccagac atgataagat     1920
acattgatga gtttggacaa accacaacta gaatgcagtg aaaaaaatgc tttatttgtg     1980
aaatttgtga tgctattgct ttatttgtaa ccattataag ctgcaataaa caagttaaca     2040
acaacaattg cattcatttt atgtttcagg ttcaggggga ggtgtgggag gttttttaaa     2100
gcaagtaaaa cctctacaaa tcaagctggg caagctagat ctagcttggc gtaatcatgg     2160
tcatagctgt ttcctgtgtg aaattgttat ccgctcacaa ttccacacaa catacgagcc     2220
ggaagcataa agtgtaaagc ctggggtgcc taatgagtga gctaactcac attaattgcg     2280
ttgcgctcac tgcccgcttt ccagtcggga aacctgtcgt gccagctgca ttaatgaatc     2340
ggccaacgcg cggggagagg cggtttgcgt attgggcgct cttccgcttc ctcgctcact     2400
gactcgctgc gctcggtcgt tcggctgcgg cgagcggtat cagctcactc aaaggcggta     2460
atacggttat ccacagaatc aggggataac gcaggaaaga acatgtgagc aaaaggccag     2520
caaaaggcca ggaaccgtaa aaaggccgcg ttgctggcgt ttttccatag gctccgcccc     2580
cctgacgagc atcacaaaaa tcgacgctca agtcagaggt ggcgaaaccc gacaggacta     2640
taaagatacc aggcgtttcc ccctggaagc tccctcgtgc gctctcctgt tccgaccctg     2700
ccgcttaccg gatacctgtc cgcctttctc ccttcgggaa gcgtggcgct ttctcaatgc     2760
tcacgctgta ggtatctcag ttcggtgtag tcgttcgct ccaagctggg ctgtgtgcac     2820
gaaccccccg ttcagcccga ccgctgcgcc ttatccggta actatcgtct tgagtccaac     2880
ccggtaagac acgacttatc gccactggca gcagccactg gtaacaggat tagcagagcg     2940
aggtatgtag gcggtgctac agagttcttg aagtggtggc ctaactacgg ctacactaga     3000
aggacagtat ttggtatctg cgctctgctg aagccagtta ccttcggaaa aagagttggt     3060
```

```
agctcttgat ccggcaaaca aaccaccgct ggtagcggtg gttttttgt ttgcaagcag    3120 cagattacgc gcagaaaaaa aggatctcaa gaagatcctt tgatcttttc tacgggtgtc    3180
gacgctcagt ggaacgaaaa ctcacgttaa gggattttgg tcatgagatt atcaaaaagg    3240
atcttcacct agatcctttt aaattaaaaa tgaagtttta atcaatcta aagtatatat    3300 gagtaaactt ggtctgacag ttaccaatgc ttaatcagtg aggcacctat ctcagcgatc    3360
tgtctatttc gttcatccat agttgcctga ctccccgtcg tgtagataac tacgatacgg    3420
gagggcttac catctggccc cagtgctgca atgataccgc gagacccacg ctcaccggct    3480
ccagatttat cagcaataaa ccagccagcc ggaagggccg agcgcagaag tggtcctgca    3540
actttatccg cctccatcca gtctattaat tgttgccggg aagctagagt aagtagttcg    3600
ccagttaata gtttgcgcaa cgttgttgcc attgctacag gcatcgtggt gtcacgctcg    3660
tcgtttggta tggcttcatt cagctccggt tcccaacgat caaggcgagt tacatgatcc    3720
cccatgttgt gcaaaaaagc ggttagctcc ttcggtcctc cgatcgttgt cagaagtaag    3780
ttggccgcag tgttatcact catggttatg gcagcactgc ataattctct tactgtcatg    3840
ccatccgtaa gatgcttttc tgtgactggt gagtactcaa ccaagtcatt ctgagaatag    3900
tgtatgcggc gaccgagttg ctcttgcccg gcgtcaatac gggataatac cgcgccacat    3960
agcagaactt taaaagtgct catcattgga aaacgttctt cggggcgaaa actctcaagg    4020
atcttaccgc tgttgagatc cagttcgatg taacccactc gtgcacccaa ctgatcttca    4080
gcatctttta ctttcaccag cgtttctggg tgagcaaaaa caggaaggca aaatgccgca    4140
aaaaagggaa taagggcgac acggaaatgt tgaatactca tactcttcct ttttcaatat    4200
tattgaagca tttatcaggg ttattgtctc atgagcggat acatatttga atgtatttag    4260
aaaaataaac aaatagggt tccgcgcaca tttccccgaa aagtgccacc tgacgtctaa    4320
gaaaccatta ttatcatgac attaacctat aaaaataggc gtatcacgag gccctttcgt    4380
ctcgcgcgtt tcggtgatga cggtgaaaac ctctgacaca tgcagctccc ggagacggtc    4440
acagcttgtc tgtaagcgga tgccgggagc agacaagccc gtcagggcgc gtcagcgggt    4500
gttggcgggt gtcggggctg gcttaactat gcggcatcag agcagattgt actgagagtg    4560
caccatatgc ggtgtgaaat accgcacaga tgcgtaagga gaaaataccg catcaggcgc    4620
cattcgccat tcaggctgcg caactgttgg gaagggcgat cggtgcgggc ctcttcgcta    4680
ttacgccagc tggcgaaagg gggatgtgct gcaaggcgat taagttgggt aacgccaggg    4740
ttttcccagt cacgacgttg taaaacgacg gccagt                              4776
```

<210> SEQ ID NO 2
<211> LENGTH: 12
<212> TYPE: PRT
<213> ORGANISM: Artificial sequence
<220> FEATURE:
<223> OTHER INFORMATION: Synthetically generated peptide

<400> SEQUENCE: 2

Met Lys Asp Pro Thr Cys Arg Phe Gly Lys Leu Ala
 1               5                  10

<210> SEQ ID NO 3
<211> LENGTH: 21
<212> TYPE: PRT
<213> ORGANISM: Artificial sequence
<220> FEATURE:
<223> OTHER INFORMATION: Synthetically generated peptide -continued

```
<400> SEQUENCE: 3

Met Glu Lys Tyr Ile Thr Glu Asn Arg Glu Val Gln Ile Lys Val Arg
 1               5                  10                  15

Asn Arg Trp Asn Ser
            20

<210> SEQ ID NO 4
<211> LENGTH: 8
<212> TYPE: PRT
<213> ORGANISM: Artificial sequence
<220> FEATURE:
<223> OTHER INFORMATION: Synthetically generated peptide

<400> SEQUENCE: 4

Met Gly Gln Thr Gly Tyr Leu Trp
 1               5

<210> SEQ ID NO 5
<211> LENGTH: 13
<212> TYPE: PRT
<213> ORGANISM: Artificial sequence
<220> FEATURE:
<223> OTHER INFORMATION: Synthetically generated peptide

<400> SEQUENCE: 5

Met Glu Gln Leu Asn Met Gly Gln Thr Gly Tyr Leu Trp
 1               5                  10

<210> SEQ ID NO 6
<211> LENGTH: 12
<212> TYPE: PRT
<213> ORGANISM: Artificial sequence
<220> FEATURE:
<223> OTHER INFORMATION: Synthetically generated peptide

<400> SEQUENCE: 6

Met Val Pro Arg Cys Gly Pro Ala Leu Ser Ser Phe
 1               5                  10

<210> SEQ ID NO 7
<211> LENGTH: 10
<212> TYPE: PRT
<213> ORGANISM: Artificial sequence
<220> FEATURE:
<223> OTHER INFORMATION: Synthetically generated peptide

<400> SEQUENCE: 7

Met Phe Pro Gly Cys Pro Lys Asp Leu Lys
 1               5                  10

<210> SEQ ID NO 8
<211> LENGTH: 15
<212> TYPE: PRT
<213> ORGANISM: Artificial sequence
<220> FEATURE:
<223> OTHER INFORMATION: Synthetically generated peptide

<400> SEQUENCE: 8

Met Val Glu Val Arg Cys Gly Arg Leu Glu Ile Trp Pro Tyr Thr
 1               5                  10                  15

<210> SEQ ID NO 9
<211> LENGTH: 24
<212> TYPE: PRT
<213> ORGANISM: Artificial sequence
<220> FEATURE:
```

<223> OTHER INFORMATION: Synthetically generated peptide

<400> SEQUENCE: 9

Met Thr Ser Thr Leu Pro Phe Ser Pro Gln Val Ser Thr Pro Arg Ser
1               5                   10                  15

Asn Arg Ile Arg Ala Pro Pro Arg
            20

<210> SEQ ID NO 10
<211> LENGTH: 233
<212> TYPE: PRT
<213> ORGANISM: Artificial sequence
<220> FEATURE:
<223> OTHER INFORMATION: Synthetically generated peptide

<400> SEQUENCE: 10

Met Asp Cys Leu Thr Asn Leu Arg Ser Ala Glu Gly Lys Val Asp Gln
1               5                   10                  15

Ala Ser Lys Ile Leu Ile Leu Val Ala Trp Trp Gly Phe Gly Thr
            20                  25                  30

Thr Ala Glu Val Ser Thr Ala Gly Ser Gly Gly Gly Ser Gly Gly
                35                  40                  45

Gly Ser Gly Gly Gly Ser Gly Gly Gly Ser Gly Ala Ser Pro
        50                  55                  60

Val Gln Phe Ile Pro Leu Leu Val Gly Leu Gly Ile Ser Gly Ala Thr
65                  70                  75                  80

Leu Ala Gly Gly Thr Gly Leu Gly Val Ser Val His Thr Tyr His Lys
                85                  90                  95

Leu Ser Ala Asn Gln Leu Ile Glu Asp Val Gln Ala Leu Ser Gly Thr
            100                 105                 110

Ile Asn Asp Leu Gln Asp Gln Ile Asp Ser Leu Ala Glu Val Val Leu
        115                 120                 125

Gln Asn Arg Arg Gly Leu Asp Leu Leu Thr Ala Glu Gln Gly Gly Ile
    130                 135                 140

Cys Leu Ala Leu Gln Glu Lys Cys Cys Phe Tyr Ala Asn Lys Ser Gly
145                 150                 155                 160

Ile Val Arg Asp Lys Ile Arg Lys Leu Gln Glu Asp Leu Ile Glu Arg
                165                 170                 175

Lys Arg Ala Leu Tyr Asp Asn Pro Leu Trp Ser Gly Leu Asn Gly Phe
            180                 185                 190

Leu Pro Tyr Leu Leu Pro Leu Leu Gly Pro Leu Phe Gly Leu Ile Leu
        195                 200                 205

Phe Leu Thr Leu Gly Pro Cys Ile Met Lys Thr Leu Thr Arg Ile Ile
210                 215                 220

His Asp Lys Ile Gln Ala Val Lys Ser
225                 230

<210> SEQ ID NO 11
<211> LENGTH: 14
<212> TYPE: PRT
<213> ORGANISM: Artificial sequence
<220> FEATURE:
<223> OTHER INFORMATION: Synthetically generated peptide

<400> SEQUENCE: 11

Met Asp Thr Leu Gly Val Arg Trp Ser Lys Asn Ser Arg Val
1               5                   10

```
<210> SEQ ID NO 12
<211> LENGTH: 15
<212> TYPE: PRT
<213> ORGANISM: Artificial sequence
<220> FEATURE:
<223> OTHER INFORMATION: Synthetically generated peptide

<400> SEQUENCE: 12

Met Tyr Lys Ser Ser Gly Glu Cys Gly Arg Gly Leu Arg Arg Pro
 1               5                  10                  15

<210> SEQ ID NO 13
<211> LENGTH: 16
<212> TYPE: PRT
<213> ORGANISM: Artificial sequence
<220> FEATURE:
<223> OTHER INFORMATION: Synthetically generated peptide

<400> SEQUENCE: 13

Met Ile Arg Tyr Ile Asp Glu Phe Gly Gln Thr Thr Thr Arg Met Gln
 1               5                  10                  15

<210> SEQ ID NO 14
<211> LENGTH: 4
<212> TYPE: PRT
<213> ORGANISM: Artificial sequence
<220> FEATURE:
<223> OTHER INFORMATION: Synthetically generated peptide

<400> SEQUENCE: 14

Met Leu Tyr Leu
 1

<210> SEQ ID NO 15
<211> LENGTH: 7
<212> TYPE: PRT
<213> ORGANISM: Artificial sequence
<220> FEATURE:
<223> OTHER INFORMATION: Synthetically generated peptide

<400> SEQUENCE: 15

Met Leu Leu Leu Leu Tyr Leu
 1               5

<210> SEQ ID NO 16
<211> LENGTH: 12
<212> TYPE: PRT
<213> ORGANISM: Artificial sequence
<220> FEATURE:
<223> OTHER INFORMATION: Synthetically generated peptide

<400> SEQUENCE: 16

Met Phe Gln Val Gln Gly Glu Val Trp Glu Val Phe
 1               5                  10

<210> SEQ ID NO 17
<211> LENGTH: 26
<212> TYPE: PRT
<213> ORGANISM: Artificial sequence
<220> FEATURE:
<223> OTHER INFORMATION: Synthetically generated peptide

<400> SEQUENCE: 17

Met Val Ile Ala Val Ser Cys Val Lys Leu Leu Ser Ala His Asn Ser
 1               5                  10                  15

Thr Gln His Thr Ser Arg Lys His Lys Val
                20                  25
```

<210> SEQ ID NO 18
<211> LENGTH: 49
<212> TYPE: PRT
<213> ORGANISM: Artificial sequence
<220> FEATURE:
<223> OTHER INFORMATION: Synthetically generated peptide

<400> SEQUENCE: 18

Met Ser Glu Leu Thr His Ile Asn Cys Val Ala Leu Thr Ala Arg Phe
1               5                   10                  15

Pro Val Gly Lys Pro Val Val Pro Ala Ala Leu Met Asn Arg Pro Thr
            20                  25                  30

Arg Gly Glu Arg Arg Phe Ala Tyr Trp Ala Leu Phe Arg Phe Leu Ala
        35                  40                  45

His

<210> SEQ ID NO 19
<211> LENGTH: 4
<212> TYPE: PRT
<213> ORGANISM: Artificial sequence
<220> FEATURE:
<223> OTHER INFORMATION: Synthetically generated peptide

<400> SEQUENCE: 19

Met Leu Thr Leu
1

<210> SEQ ID NO 20
<211> LENGTH: 9
<212> TYPE: PRT
<213> ORGANISM: Artificial sequence
<220> FEATURE:
<223> OTHER INFORMATION: Synthetically generated peptide

<400> SEQUENCE: 20

Met Arg Leu Ser Lys Arg Ile Phe Thr
1               5

<210> SEQ ID NO 21
<211> LENGTH: 11
<212> TYPE: PRT
<213> ORGANISM: Artificial sequence
<220> FEATURE:
<223> OTHER INFORMATION: Synthetically generated peptide

<400> SEQUENCE: 21

Met Ser Lys Leu Gly Leu Thr Val Thr Asn Ala
1               5                   10

<210> SEQ ID NO 22
<211> LENGTH: 70
<212> TYPE: PRT
<213> ORGANISM: Artificial sequence
<220> FEATURE:
<223> OTHER INFORMATION: Synthetically generated peptide

<400> SEQUENCE: 22

Met Arg Cys Glu Ile Pro His Arg Cys Val Arg Arg Lys Tyr Arg Ile
1               5                   10                  15

Arg Arg His Ser Pro Phe Arg Leu Arg Asn Cys Trp Glu Gly Arg Ser
            20                  25                  30

Val Arg Ala Ser Ser Leu Leu Arg Gln Leu Ala Lys Gly Gly Cys Ala
        35                  40                  45

```
Ala Arg Arg Leu Ser Trp Val Thr Pro Gly Phe Ser Gln Ser Arg Arg
         50                  55                  60

Cys Lys Thr Thr Ala Ser
 65                  70

<210> SEQ ID NO 23
<211> LENGTH: 88
<212> TYPE: PRT
<213> ORGANISM: Artificial sequence
<220> FEATURE:
<223> OTHER INFORMATION: Synthetically generated peptide

<400> SEQUENCE: 23

Met Ile Pro Arg Asp Pro Arg Ser Pro Ala Pro Asp Leu Ser Ala Ile
 1               5                  10                  15

Asn Gln Pro Ala Gly Arg Ala Glu Arg Arg Ser Gly Pro Ala Thr Leu
             20                  25                  30

Ser Ala Ser Ile Gln Ser Ile Asn Cys Cys Arg Glu Ala Arg Val Ser
         35                  40                  45

Ser Ser Pro Val Asn Ser Leu Arg Asn Val Val Ala Ile Ala Thr Gly
     50                  55                  60

Ile Val Val Ser Arg Ser Ser Phe Gly Met Ala Ser Phe Ser Ser Gly
 65                  70                  75                  80

Ser Gln Arg Ser Arg Arg Val Thr
                 85

<210> SEQ ID NO 24
<211> LENGTH: 56
<212> TYPE: PRT
<213> ORGANISM: Artificial sequence
<220> FEATURE:
<223> OTHER INFORMATION: Synthetically generated peptide

<400> SEQUENCE: 24

Met Leu Cys Lys Lys Ala Val Ser Ser Phe Gly Pro Pro Ile Val Val
 1               5                  10                  15

Arg Ser Lys Leu Ala Ala Val Leu Ser Leu Met Val Met Ala Ala Leu
             20                  25                  30

His Asn Ser Leu Thr Val Met Pro Ser Val Arg Cys Phe Ser Val Thr
         35                  40                  45

Gly Glu Tyr Ser Thr Lys Ser Phe
     50                  55

<210> SEQ ID NO 25
<211> LENGTH: 49
<212> TYPE: PRT
<213> ORGANISM: Artificial sequence
<220> FEATURE:
<223> OTHER INFORMATION: Synthetically generated peptide

<400> SEQUENCE: 25

Met Arg Arg Pro Ser Cys Ser Cys Pro Ala Ser Ile Arg Asp Asn Thr
 1               5                  10                  15

Ala Pro His Ser Arg Thr Leu Lys Val Leu Ile Ile Gly Lys Arg Ser
             20                  25                  30

Ser Gly Arg Lys Leu Ser Arg Ile Leu Pro Leu Leu Arg Ser Ser Ser
         35                  40                  45

Met
```

<210> SEQ ID NO 26
<211> LENGTH: 6
<212> TYPE: PRT
<213> ORGANISM: Artificial sequence
<220> FEATURE:
<223> OTHER INFORMATION: Synthetically generated peptide

<400> SEQUENCE: 26

Met Pro Gln Lys Arg Glu
 1               5

<210> SEQ ID NO 27
<211> LENGTH: 27
<212> TYPE: PRT
<213> ORGANISM: Artificial sequence
<220> FEATURE:
<223> OTHER INFORMATION: Synthetically generated peptide

<400> SEQUENCE: 27

Met Leu Asn Thr His Thr Leu Pro Phe Ser Ile Leu Leu Lys His Leu
 1               5                  10                  15

Ser Gly Leu Leu Ser His Glu Arg Ile His Ile
             20                  25

<210> SEQ ID NO 28
<211> LENGTH: 5
<212> TYPE: PRT
<213> ORGANISM: Artificial sequence
<220> FEATURE:
<223> OTHER INFORMATION: Synthetically generated peptide

<400> SEQUENCE: 28

Met Tyr Leu Glu Lys
 1               5

<210> SEQ ID NO 29
<211> LENGTH: 26
<212> TYPE: PRT
<213> ORGANISM: Artificial sequence
<220> FEATURE:
<223> OTHER INFORMATION: Synthetically generated peptide

<400> SEQUENCE: 29

Met Thr Leu Thr Tyr Lys Asn Arg Arg Ile Thr Arg Pro Phe Arg Leu
 1               5                  10                  15

Ala Arg Phe Gly Asp Asp Gly Glu Asn Leu
             20                  25

<210> SEQ ID NO 30
<211> LENGTH: 11
<212> TYPE: PRT
<213> ORGANISM: Artificial sequence
<220> FEATURE:
<223> OTHER INFORMATION: Synthetically generated peptide

<400> SEQUENCE: 30

Met Gln Leu Pro Glu Thr Val Thr Ala Cys Leu
 1               5                  10

<210> SEQ ID NO 31
<211> LENGTH: 31
<212> TYPE: PRT
<213> ORGANISM: Artificial sequence
<220> FEATURE:
<223> OTHER INFORMATION: Synthetically generated peptide

<400> SEQUENCE: 31

-continued

```
Met Pro Gly Ala Asp Lys Pro Val Arg Ala Arg Gln Arg Val Leu Ala
 1               5                  10                  15
Gly Val Gly Ala Gly Leu Thr Met Arg His Gln Ser Arg Leu Tyr
                20                  25                  30

<210> SEQ ID NO 32
<211> LENGTH: 51
<212> TYPE: DNA
<213> ORGANISM: Artificial sequence
<220> FEATURE:
<223> OTHER INFORMATION: Synthetically generated primer

<400> SEQUENCE: 32
gggccctcgc gagcggccca gccggccgac atcaagatga cccagtctcc a            51

<210> SEQ ID NO 33
<211> LENGTH: 45
<212> TYPE: DNA
<213> ORGANISM: Artificial sequence
<220> FEATURE:
<223> OTHER INFORMATION: Synthetically generated primer

<400> SEQUENCE: 33
gggccctcgc gatgcggccg ctgaggagac tgtgagagtg gtgcc                   45

<210> SEQ ID NO 34
<211> LENGTH: 47
<212> TYPE: DNA
<213> ORGANISM: Artificial sequence
<220> FEATURE:
<223> OTHER INFORMATION: Synthetically generated primer

<400> SEQUENCE: 34
ggaaattcca tatggaattc ccgttacata acttacgggt aaatggc                 47

<210> SEQ ID NO 35
<211> LENGTH: 39
<212> TYPE: DNA
<213> ORGANISM: Artificial sequence
<220> FEATURE:
<223> OTHER INFORMATION: Synthetically generated primer

<400> SEQUENCE: 35
ggaattccat atggaattcc tcagtcctgc tcctcggcc                          39
```

CELL-SPECIFIC RETROVIRAL VECTORS WITH ANTIBODY DOMAINS AND METHOD FOR THE PRODUCTION THEREOF FOR SELECTIVE GENE TRANSFER

RELATED APPLICATIONS

This application is a continuation (and claims the benefit of priority under 35 USC 120) of U.S. Ser. No. 09/555,350, (now abandoned), having a filing date of Aug. 24, 2000, which is a National Stage application of International Application No. PCT/DE98/03543, which was filed Nov. 27, 1998, and published by mention of grant on Jul. 3, 2002, as EP Patent No. 1 034 292 B1. The International application claims the benefit of the filing date of German Application No. DE 197 52 854.6, which was filed on Nov. 28, 1997, and published by mention of grant on Jul. 6, 2000, as German Patent No. 197 52 854 C2, all of which are herein incorporated by reference.

FIELD OF THE INVENTION

The present invention relates to cell-specific retroviral vectors with antibody recognition domains (scFv) which are suitable for cell-specific transduction of a selected mammalian cell type (cell targeting), methods for the preparation of the cell-specific retroviral vectors and their use for the gene transfer into selected cells. The invention further relates to retroviral packaging cells to obtain the cell-specific retroviral vectors of the present invention.

BACKGROUND OF THE INVENTION

The majority of retroviral vectors which are presently used in gene therapeutic research are derived from the amphotropic murine leukemia virus (MLV). The host cell range of the amphotropic MLV is determined by the surface envelope protein (SU) encoded by the env gene. The protein products of the env gene form the outer envelope of the retroviral vector. The SU proteins interact with, i.e. bind to a specific protein (receptor) on the surface of the host cell. The env gene products of the amphotropic MLV enable gene transfer into a great number of different mammalian cells. However, a selective gene transfer in particular cell or tissue types of humans or other mammals is not possible, since the receptor for the MLV envelope proteins on the surface of mammalian cells, which mediates the entry of amphotropic MLV vectors and gene transfer, is found on nearly all of these cells. Accordingly, the host cell range of the amphotropic MLV is not specific.

A host cell specificity, however, is advantageous e.g. for gene therapeutic use, since in a gene therapy outside of the organism (ex vivo) (Anderson et al., Science 256 (1992) 808-813; Yu et al., H. Gene Therapy 8 (1997) 1065-1072) laborious purifications of cells are avoided. It is desired for therapeutic, diagnostic or vaccination use in vivo, that retroviral vectors are targeted specifically to the desired host cells and subsequently transfer the therapeutic gene. By modification of the surface envelope protein a restriction of the host cell range of the amphotropic MLV could be achieved. A modification of the surface capsid protein was done by fusion with a hormone domain. A transduction of the cells carrying the specific hormone receptor occurred (Kasahara et al., Science 266 (1994) 1373-1375). Further, the surface envelope protein was modified by fusion with a single chain antibody fragment (single chain variable fragment, in the following referred to as "scFv"). The fragment represented the antigen binding domain of an antibody and is a fusion protein composed of the variable domains Vh and Vl of a monoclonal antibody. Both domains are linked via a glycine and serine oligopeptide [-(ser-gly4)3-gly-)] which enables the correct folding of the fusion protein (Huston et al., Methods Enzymol. 203 (1991) 46-88, Whitlow et al., Methods: A companion to Methods Enzymol. 2 (1991) 97-105). All modifications of the MLV surface capsid protein using a scFv carried out so far showed that while binding of the vectors to the host target cell occurred, however, there was no entry into the cell (Russel et al., Nucleic Acid Res. 21 (1993) 1081-1085). Furthermore it is known that the surface envelope protein of the MLV generally does not enable for extensive modifications (Cosset et al., J. Virol. 69 (1995) 6314-632). Modifications in which a portion of the binding domain of the MLV-SU protein has been replaced led to an incorrect processing and, thus, to a defective transport of the SU protein to the cell surface (Weiss et al., In J. A. Levy (ed.) The Retroviridae 2 (1993) 1-108; Morgan et al., J. Virol. 67 (1993) 4712-4721; Russel et al., Nucleic Acid Res. 21 (1993) 1081-1085). Accordingly, the development of cell-specific retroviral vectors on the basis of MLV with modified surface envelope proteins is only little promising.

Retroviral vectors on the basis of spleen necrosis virus SNV are more suitable for a targeted gene transfer into e.g. human cells, since the surface envelope protein of SNV enables for extensive modifications after which still correct processing occurs (Martinez and Dornburg, Virol. 208 (1995) 234-241; Chu et al., Gene Therapy 1 (1994) 292-299; Chu and Dornburg J. Virol. 69 (1995) 2659-2663). At least two components are required for the preparation of such vectors. On the one hand a so-called expression construct is to be prepared enabling packaging in and transfer through a retrovirus. The expression construct comprises a coding DNA fragment of the desired gene product, e.g. a gene for gene therapy or as a vaccine. The expression construct has to comprise a nucleotide sequence which is referred to as packaging signal psi ($\psi$) and controls the efficient packaging of mRNA in retroviral particles. Furthermore a packaging or helper cell is required which provides the gag, pol and env gene products of SNV, without packaging of the gag, pol and env genes into a retrovirus. The gag, pol and env genes which are present in the packaging cell have to be psi-negative. Following transduction of the expression construct by means of transfection of the respective plasmid DNA into the packaging cells, retroviral particles are released into the cell culture supernatant, which particles contain the expression construct and are only able to transduct said construct but not the gag, pol and env genes into the target cell. Said vectors are replication incompetent and only pass one cycle of replication. The general method for the preparation of replication incompetent retroviral vectors is known in the prior art (Weiss et al., In J. A. Levy (ed.). The Retroviridae 2 (1993) 1-108; Morgan et al., J. Virol. 67 (1993) 4712-4721; Russel et al., Nucleic Acid Res. 21 (1993) 1081-1085; Cosset et al., J. Virol 69 (1995); Martinez and Dornburg, Virol. 208 (1995) 234-241; Chu et al., Gene Therapy 1 (1994) 292-299; Chu and Dornburg, J. Virol. 69 (1995) 2659-2663).

The tropism (host cell specificity) of spleen necrosis virus is determined by the surface envelope protein (SU protein) encoded by the env gene of SNV. The wild type SNV surface envelope protein does not allow for a selective gene transfer into particular human cells or tissues since the specific acceptor protein (receptor) is not present on the surface of human cells (Dornburg, Gene Therapy 2 (1995) 1-10). Therefore, a method has been developed to substitute the SU protein of SNV by the antigen recognizing domains of antibodies. Said [SNV-scFv-Env] vectors with the two different scFv known heretofore were able to transmit the psi positive reporter gene, bacterial $\beta$-galactosidase, into the selected human target cells. Said scFv are directed against the hapten dinitrophenol (DNP) or against an unknown surface molecule on colon CA cells and other cancer cells, respectively. (Chu et al., Gene Therapy 1 (1994) 292-299, Chu et al., BioTechniques 18

(1995) 890-899; Chu and Dornburg, J. Virol. 71 (1997) 720-725). A packaging cell line (DSH-CXL) has been developed, containing the psi-negative SNV genes gag, pol and env as well as the psi-positive reporter gene expression construct (pCXL). Following transfection of the packaging cell using plasmid DNA of another env expression gene (pTC53), in which the entire surface envelope protein was substituted by a single chain antibody fragment (scFv), retroviral vectors were released into the cell supernatant which in addition to the wild type surface envelope protein also carried the chimeric [scFv-Env] surface protein on their surface. By means of said vectors the reporter gene could be transferred into the target cells specific for scFv, canine osteosarcoma cells (D17), which were conjugated with DNP, or HeLA cells (human cervical carcinoma cells), respectively. However, this method described for the preparation of cell-specific retroviral vectors has the disadvantage that only already known and cloned scFv may be used. Further, it has been found by us that not every scFv is suitable as a portion of a [SNV-scFv-Env] vector for cell transduction (transfer of the desired gene to the target cell).

SUMMARY OF THE INVENTION

Generally, the gene transfer into mammalian cells by means of retroviruses has the following benefits:

- Normally, one copy of the desired gene is transferred into the mammalian cell.
- Generally, the desired gene is transferred without mutation or rearrangements.
- Stable introduction of the desired gene into the genome of the target cell occurs.

Furthermore, it is desired that the retroviral vector has a particular cell-specificity by which e.g. the therapeutic gene may be introduced into a selected cell population.

Therefore, it is an object of the present invention to provide cell-specific retroviral vectors having antibody recognition domains for selective gene transfer into mammalian cells as well as a universal method for the preparation thereof. It is possible to improve the gene transfer by means of said vectors. A further object of the invention is to provide retroviral packaging cells for obtaining the vectors according to the present invention. The solution of said objects is obvious from the claims, the following description and the figures.

The object is solved by the method of the present invention for the preparation of cell-specific retroviral vectors comprising the following steps of: a) Immunizing a mammal with one or more cell population(s), b) Isolation of RNA from the mammal immunized, comprising the B cell RNA, c) preparation of cDNA portions of the variable regions of the immunoglobulin heavy and light chains from the isolated RNA by means of RT-PCR using primers for the immunoglobulin heavy and light chain wherein the primers comprise the nucleic acid sequence for an oligopeptide linker, d) ligation of the cDNA portions to scFv-cDNAs, e) ligation of the scFv-cDNAs into a phagemid vector and transformation of a host bacterium with said phagemid vector, f) isolation of phages which bind to the cell population(s) used in step a) by means of selection, g) isolation of cell-specific phages from the phages obtained in step f) which only bind to the cell population(s) used in step a) by means of selection, h) excising the scFv encoding DNA fragments from the cell-specific phages obtained in step g) and ligation into a psi-negative retroviral Env expression vector, i) transformation of the resulting Env-scFv expression vector into a packaging cell, and j) isolation of retroviral vectors secreted from the packaging cell.

Optionally, the method according to the present invention comprises further isolation of cell-specific phages obtained in step g). Optionally, the method of the invention further comprises the step: k) isolation of retroviral vectors secreted by the packaging cell, which transduce the cells of the cell population(s) by means of selection. Furthermore, the steps f) and/or g) may be repeated at least once.

A method is preferred in which the immunized mammal is selected from the group consisting of mouse, rat, guinea pig, rabbit, goat or sheep. Also preferred is a method in which the cell population(s) is/are selected from the group consisting of man, mouse, rat, sheep, cattle or pig. Particularly preferred is a method, in which the cell population(s) is/are selected from the group consisting of T cells, epithelial cells, muscle cells, stem cells, neural cells, hematopoietic cells, carcinoma cells or liver cells. A method is preferred in which the env gene is derived from spleen necrosis virus (SNV). Particularly preferred is a method in which the expression vector is the vector with the designation pTC53.

The cell-specific retroviral vectors obtainable by means of the method of the invention may be used as medicaments. Preferred is the use for the preparation of a medicament for gene therapy, vaccination therapy or diagnostics. Particularly preferred is the therapy of cystic fibrosis, ADA deficiency, HIV infections, leukemia, chronic granulomatosis.

Furthermore, the invention is solved by the provision of retroviral packaging cells for obtaining retroviral vectors of the invention, transformed both with one or more psi-negative expression construct(s) expressing gag, pol and/or env gene products and with a psi-negative Env-scFv expression construct according to claim 1h). A packaging cell is preferred further comprising a psi-positive expression construct comprising a nucleic acid fragment, which is to be introduced into the cell to be transduced by the retroviral vector. Particularly preferred is a packaging cell wherein the nucleic acid fragment comprises a therapeutic gene or its DNA fragment and/or a reporter gene. Particularly preferred is a packaging cell wherein the therapeutic gene or its nucleic acid fragment comprises CFTR, phox91, ADA, IL-16, p53 or revM10 gene or vaccination genes, e.g. recombinant gp120 and IL-16. Further particularly preferred is a packaging cell wherein the reporter gene comprises β-galactosidase, green fluorescent protein, luciferase or neomycin.

Other features and advantages of the invention will be apparent from the following detailed description, and from the claims.

BRIEF DESCRIPTION OF THE DRAWINGS

The figures are meant to illustrate the invention.

FIG. 1 schematically shows the ENV-scFv expression construct pTC53, pT-scFv and pT/zeo, the transfection thereof into the packaging cell DSH-CXL which secretes the vectors of the present invention.

FIG. 2 schematically shows the preparation, isolation and selection of the vectors of the invention.

FIG. 3 is a schematic illustration of an immunoglobulin and the scFv resulting therefrom. Furthermore, scFv display phages and SNV-scFv-Env vectors are schematically depicted.

FIG. 4 shows the nucleic acid sequence of pTC53 (SEQ ID NO:1) and amino acids encoded thereby (SEQ ID NOs:2-21, 23-31, and 22, respectively).

DETAILED DESCRIPTION

The term amphotropic virus used means infection and replication in murine and human cells, in contrast to an ecotropic virus which only replicates in murine cells. The term retroviral vector used herein means replication deficient retroviral virus particle which instead of retroviral mRNA may transmit a foreign introduced RNA of a gene, e.g. of a therapeutic gene or a fragment thereof or of a reporter gene. The term antibody recognition domain (scFv) used herein means an antigen binding site of an antibody comprising Vh and Vl chain. The term SNV used herein represents spleen necrosis virus with its strains and substrains. SNV belongs to the avian reticolo endotheliosis viruses (REV), type D retrovirus.

To provide the cell-specific antibody recognition domains (scFv) a new combinatory phage cDNA library of the variable domains of the light and heavy chains of the immunoglobulins is prepared. For this purpose, a mammal, e.g. a mouse, rat, rabbit, guinea pig, goat or sheep is immunized with a sufficient titer of one or more cell population(s) in a usual manner. The cell population is the cell type forming a surface receptor to which the retroviral vectors of the present invention specifically bind. The cells may be derived from a mammal which is different from the mammal to be immunized, e.g. from human, mouse, rat, sheep, cattle or pig. The cells may be such cells in which for example a somatic gene therapy, a vaccination therapy or diagnostics is to be carried out. Typical examples of such cells are T-cells, liver cells, muscle cells, neural cells, fibroblasts, epithelial cells, stem cells or hematopoietic cells. For immunization one or more cell population(s) may be simultaneously administered to the mammal depending on the cell population(s) for which the retroviral vector of the present invention has to be specific.

For the preparation of a cDNA library B cell RNA of the immunized mammal is first isolated in a known manner. The mRNA sequences of the regions of the heavy and light chain ($V_H$ and $V_L$) of the immunoglobulins responsible for antigen recognition, are transcribed into cDNA and amplified in a usual manner by means of reverse transcription and subsequent polymerase chain amplification. The primer pairs and their sequences for $V_H$ and $V_L$ regions are known to the person skilled in the art. For example, they are contained in the kit commercially available from Pharmacia company, or may be obtained from known data bases (EMBL), respectively. It is known to the skilled artisan that he has to use different primer sequences for every immunized mammalian species. The sequences are also contained in the known data bases. The cDNA fragments of the $V_H$ and $V_L$ regions are then linked to scFv-cDNAs by means of a ligase reaction in a usual manner. It is obvious to the skilled artisan that during ligation different combinations of cDNA fragments are prepared. The resulting scFv-cDNAs may then be cloned into a phagemid vector, e.g. pCANTA 5E phagemid, Pharmacia company. Subsequently, host bacteria, e.g. *E. coli* TG1 are transformed with the phagemid vector.

The recombinant phages produced by the bacteria are then isolated in a usual manner and selected for the presence of cell-specific scFv peptides. The phages are then contacted in a usual manner with the cell population(s) which have been used for immunization. Phages not binding to cells do not carry a specific scFv peptide and are removed by means of washing steps in a usual manner. Phages binding to the cells present the desired scFv peptide on their surface and are eluted in a usual manner. Phages presenting the desired scFv peptide are amplified by allowing them to infect host bacteria in a usual manner. This selection step may be repeated once or several times to enrich the binding phages. This procedure is referred to as panning. The phages are subjected to a further selection after panning or directly after the first selection step. For this purpose the phages are contacted with one or more other cell population(s) which are different from the cells used for immunization. Phages not binding to said cells present a cell-specific scFv peptide. They are isolated from the cell supernatant in a usual manner and are used for a host bacteria infection for amplification. Also this selection step may be repeated once or several times (Marks et al., BioTechnology 10 (1992) 779; Clackson et al., Nature 352 (1991) 624; Marks et al., J. Mol. Biol. 222 (1991) 581; Chaudhary et al., Proc. Natl. Acad. Sci USA 87 (1990) 1066; Chiswell et al., TIBTECH 10 (1992) 80: McCafferty et al., Nature 348 (1990) 552; Huston et al., Proc. Natl. Acad. Sci. USA 85 (1988) 5879).

For the preparation of the cell-specific retroviral vectors of the present invention the above described phage cDNA library is used as a starting material. The scFv-cDNAs of the phages remaining after the second selection step and the panning method which has optionally been carried out are excised in a usual manner from the phage DNA and inserted into a retroviral Env expression gene. The retroviral env expression gene may be derived from SNV. A typical example for a SNV-scFv-env expression construct is pTC53. The sequence is shown in FIG. 4. A typical example for a wild type (wt) SNV-env expression construct is pIM29.

The construction of the expression plasmids encoding wt-SNV-ENV proteins, e.g. pIM29 and the chimeric SNV-scFv-ENV proteins has been previously described by Chu et al. (J. Virol. 71 (1997) 720-725). The expression of the DNA coding for the wt-env gene is controlled by an MLV promoter. The env-cDNA was excised from a plasmid encoding the complete SNV virus via restriction sites SacII and AvrII and introduced by insert into a linker (L). To enable a correct processing of the protein pIM29 contains the polyadenylation site of Simian Virus 40 (SV 40). Thus, from this plasmid the expression of the wt-env gene may occur, so that following proteolytic cleavage of a precursor protein the outer glycoprotein (SU) and the transmembrane protein (TM) are obtained. However, other plasmids, promoter, linkers, polyadenylation signals known to the skilled artisan and further DNA elements required for a correct processing may be used.

For the expression of SNV-scFv-ENV proteins scFv obtained in a known manner are introduced into a SNV-ENV expression construct, e.g. pTC53, in a usual manner. The restriction recognition sites for the enzymes SfiI and NotI present in pTC53 enable the molecular cloning of e.g. scFv between the SNV-env-leader sequence and the DNA region encoding the transmembrane protein (TM protein). The protease cleavage site between SU and TM present in wt-ENV is deleted in pTC53, so that a fusion protein is expressed which consists of a single chain antibody fragment at the N-terminus and of the SNV-TM at the C-terminus. The regulatory elements, such as MLV promoter and SV40 polyadenylation signal are identical to those of the pIM29 vector. For enhancing the expression of a chimeric env gene an adenoviral leader sequence, e.g. Avtl (Sheay et al., BioTechiques 15 (1993) 856-861) is inserted into the expression plasmid pTC53. A zoezin cassette (pSV2zeo; Invitrogen Comp., The Netherlands) functions to select stably transfected cells, so that single cell clones may be established.

The psi-negative SNV-scFv-env expression construct may be introduced into packaging cells by means of electroporation or other known methods. A typical packaging cell is for example DSH-CXL. Further, packaging cells have psi-negative env, gag, pol expression constructs and for the desired gene transfer into the specific target cells a further psi-positive expression construct comprising for example a gene or DNA fragment for gene therapy, vaccination therapy or a reporter gene for diagnostics. Following transfection of the packaging cells a transient expression and release of retroviral vectors which present in addition to natural SU proteins recombinant SU-scFv proteins into the cell culture supernatant occurs. The retroviral vectors may then be used for transduction of the target cell, i.e. the cell population used for immunization in a usual manner. Optionally, said step may be a for selection step. Only the retroviral vectors of the invention which transduce the target cell in a sufficient manner are further employed. These vectors may be subjected to a further selection step. The vectors may be used in a conventional manner for transduction of cell populations different from the cell population used for immunizing said mammal. Thus, vectors not transducing the other cells but only the target cells may be obtained in a double selection step.

For establishing of stable packaging cell lines which constitutively release the retroviral vectors of the invention, a selection marker, e.g. the zeocin resistance gene (Invitrogen), may be inserted in a usual manner into the scFv expression on construct, e.g. pTC53. The scFv expression constructs provided with the zeocin resistance gene are transferred into the packaging cells e.g. by means of the liposome technique (lipofectamine, Gibco BRL). After a selection of about two weeks of the trasfectants in zeocin containing culture medium cell clones may be established which transduced target cell populations with a titre of about $10^4$-$10^6$ retroviral vectors pro ml depending on the scFv-cDNA fragment.

The gene transduced with the retroviral vectors of the invention into the target cell population or populations may for example be the RNA of a therapeutic gene or a fragment thereof. Therapeutic genes may for example be the CFTR gene, ADA gene, LDL receptor, β-globin, factor VIII or factor IX, dystrophin gene. The target cells in the case of the CFTR gene would be e.g. lung epithelial cells, in the case of the ADA gene the stem cells of bone marrow or T lymphocytes, for LDL receptor the liver cells, for dystrophin gene skeletal muscle cells, for β-globin gene hematopoietic stem cells, for factor VIII or factor IX fibroblasts and liver cells. It is obvious to the skilled artisan that this listing represents only a selection of therapeutic genes and other genes may also be used for a gene therapy. The DNA fragments of a therapeutic gene comprise for example antisense nucleic acids or ribozymes. Further, DNA fragments may comprise portions of a gene containing the trinucleotide repeats of e.g. the fragile X gene.

Further, the RNA of a reporter gene, e.g. β-galactosidase, GFP, luciferase or neomycin, may be introduced into the retroviral vectors of the present invention. The reporter genes enable the determination whether the target cells have been transduced with the retroviral vectors.

Further, the RNA of a gene or a fragment thereof may be transduced into the target cell for vaccination purposes. A typical vaccination gene is for example the recombinant gp120 or gp160 of HIV. The transduction of immune cells with these genes or fragments stimulates the antibody formation against viral gene products.

The vectors of the present invention may for example be applied by i.v. or i.m. injections. The packaging cells of the present invention may however be enclosed into e.g. organoids (Teflon bags), which are then implanted into the organism and secrete the vectors according to the present invention into the blood stream or tissue. Further application forms are obvious to the person skilled in the art.

The retroviral packaging cell of the invention for obtaining the pseudotyped retroviral vectors of the present invention is provided by transfecting a cell line e.g. a human cell line with psi-negative expression construct expressing the gag and pol gene products of SNV and with the psi-negative SNV-Env expression construct and/or psi-negative SNV-scFv-env expression construct in a conventional manner.

Furthermore, packaging cells may be used, which already contain the psi-negative expression constructs for gag and pol gene products. Into such packing cells only the psi-negative expression construct for the virus envelope and the psi-positive expression construct for the nucleic acid sequence to be transduced into the target cell have to be transfected. Methods for transfection of the expression constructs are known to the skilled artisan. By the packaging cells of the invention, retroviral vector particles are released into the cell supernatant which contain the expression construct, but not the constructs encoding GAG, POL and ENV proteins. Thus, only the desired e.g. therapeutic gene or reporter gene is transferred into the target cell.

The illustrated invention opens up following possibilities:
  Genes, gene fragments or other nucleic acid sequences may be transferred into selected mammalian cells.
  further enhancement of the efficiency of the nucleic acid transfer may be achieved by improvement of the env gene constructs.
  gene therapy, labeling and vaccination strategies may be developed, for which a selective nucleic acid transfer into selected mammalian cells is desirable.

The following examples illustrate the invention and are not intended to be limiting:

1. Isolation and Cloning of Cell-specific scFv

For the preparation, isolation and selection of cell-specific scFv a mouse was immunized with the human T cell line T-C8166 (Clapham et al., Virology 158 (1987) 44-51) in a conventional manner, the spleen removed and RNA was isolated. Cloning of the scFv-cDNAs was carried out with the commercially available kit of Pharmacia company according to the manufacture's instructions. The resulting phages were examined in a conventional manner with respect to their binding characteristics to target cells. There were isolated 150 phages which specifically bound to the target cells. The 150 thus obtained cell-specific scFv were used to prepare the SNV-scFv vectors according to the present invention.

2. Cloning of Specific scFV-cDNA Fragments into Env Expression Constructs

The scFc-cDNAs of 150 cell-specific scFv were excised in a usual manner from the phagemid DNA and each of the DNAs was ligated into the expression construct pTC53. pTC53 was obtained by modification of the universal eukaryotic vector pRD114 (Chu et al., J. Virol. 71 (1997) 720-725; Sheay et al., BioTechniques 15 (1993) 856-861; Chu et al., BioTechniques 18 (1995) 890-895). In this vector, the SNV-wt-env gene was deleted except for the leader sequence and the transmembrane-protein encoding cDNA. An additionally inserted spacer enables the insertion of a foreign DNA (here scFv-cDNA) following the ENV-leader sequence via the restriction recognition site NaeI. The sequence of pTC53 is shown in FIG. 4. For the insertion of the scFv-cDNA the Env-expression construct pTC53 was modified so that Sfi I and Not I specific restriction endonuclease recognition sites and inserted between the SNV-leader sequence and SNV-transmembrane sequence (T M) in a usual manner: For this purpose a recombinant PCR is carried out in a usual manner starting from the DNA of the planned PKA1558 (Scov. H. & Andersen, K. B., 1993) and the DNA coding of the anti-transferrin receptor scFv so that via Nru I (5' and 3') an insertion of the amplified fragment into the Nae I restricted pTC53 is possible. The thus inserted fragment contains the multiple Sfi I/Not I cloning site since the primers used further include a neighboring Sfi I or Not I recognition site, respectively, in addition to the terminal Nru I recognition site. For recombinant PCR the following primers were used (SEQ ID NOs:32 and 33):

```
PKATFNNRu+:
5'-GGGCCCTCGCGAGCGGCCCAGCCGGCCGACATCAAGATGACCCAGTCTCCA-3'
          Nru I         Sfi I
```

```
PKATFNRNRu-:
5'-GGGCCCTCGCGATGCGGCCGCTGAGGAGACTGTGAGAGTGGTGCC-3'
          Nru I   Not I
```

The PCR conditions were: 94° C./3 min, 94° C./1 min, 59° C./1 min. 72° C./1 min, 25 cycles, 72° C./10 min and then cooling to 4° C. The PCR fragment was gel-electophorized, extracted from the gel matrix (Quiaex, Quiagen Comp.) and ligated in a conventional manner with the plasmid pTC53 opened with Nae I.

The scFv-cDNAs from the phagemid (pCANTA 5E) were excised by means of the restriction endonucleases Sfi I and Not I. For this purpose the phagemid-plasmid DNA was prepared by means of known methods, and in each case 8 μg of plasmid DNA were digested with 60 U each of the restriction endonucleases Sfi I and Not I at 50° C. for 1.5 h and subsequently at 37° C. for 1.5 h. The reaction batch occurred in a volume of 200 μl which was supplemented with 20 μl BSA (10×conc.) and 20 μl reaction puffer 3 (10×conc.). Upon completion of the reaction period the batch was electophorized on a 1% agarose gel. Following separation the scFv-cDNA specific band (about 750 bp) was purified from the agarose gel by means of known methods.

The purified fragment was ligated with the Env expression construct pTC53 which has also been opened with the restriction endonucleases Sfi I and Not I. For this purpose equimolar amounts of the scFv-cDNA fragment and pTC53 fragment were supplemented with 200 U T4 ligase and 1.5 μl 10× ligase buffer in a 15 μl volume. The batch was incubated at 4° C. over night. To enable an efficient transformation of bacteria the bacterial strains TOP10F' and JS5 were made competent by means of a modified method according to Hanahan (1983). Following inoculation of 100 ml LB-medium with 500 μl of an overnight culture, the bacterial suspension was incubated at 37° C. up to a density ($OD_{550}$) of 0.6. Subsequently, the bacteria were chilled on ice, pelleted at 6000 rpm and 4° C. (Minifuge RF, Heraeus, Hanau) and resuspended in 40 ml TFB1 buffer (30 mM KOAc, 100 mM $RbCl_2$, 10 mM $CaCl_2$, 15% glycerol, pH 5.8, adjusted with acetic acid, thereafter filter sterilized). After an incubation period of 15 min on ice and centrifugation at 6000 rpm and 4° C. the bacterial pellet was resuspended in 4 ml of TFB2 buffer (10 mM MOPS, 75 mM $CaCl_2$, 10 mM $RbCl_2$, 15% glycerol, pH-Wert 6.5, adjusted with KOH solution, thereafter filter sterilized). The bacterial suspension was then divided into aliquots of 100 μl each and then shock frozen on dry ice. The storage was carried out at −70° C. For transformation, 100 μl of competent bacteria were thawed on ice and following addition of 1-2 μl of the respective ligation batch incubated on ice for 30 min. After a subsequent temperature shock (45 s at 42° C., thereafter 2 min on ice) the bacteria were added with 500 μl SOC medium (GIBCO/BRL, Eggenstein) and cultivated for 1 h at 37° C. for expression of antibiotic resistance in a bacterial shaker. The bacterial suspension was streaked out on LB agar plates supplemented with the antibiotic ampicillin and incubated at 37° C. over night.

The preparation of plasmids from bacteria (*E. coli* TopF10) was done with the QIAGEN plasmid kits of QIAGEN company, Hilden. For the preparation of a low amount of plasmid DNA the bacteria of a 15 ml overnight culture (LB medium with 50 μg/ml ampicillin) were lysed with the solutions provided by the manufacturer and purified via an anion exchange column (tip 20). For the preparation of large amounts of plasmid DNA (maxi preparation) 400 ml overnight cultures were prepared.

3. Selection of Retroviral Vectors

Transient transfection of the scFv-pTC53 expression constructs into the packaging cell DSH-CXL by means of electroporation: for each electroporation $2 \times 10^6$ DSH-CXL cells were resuspended in 480 μl PBS and added to a Gene-Pulser cuvette (0.4 cm electrode, gap 50, Biorad, Munich). Thereafter 20 μg of recombinant plasmid DNA were added to the cell solution. The content of the cuvette was subjected to an electric pulse in an electroporator (Gene-Pulser Apparatus, Biorad, Munich) at 270 V and 960 μF. After 10 min of incubation of the cuvette on ice the cells were added into 20 ml of fresh culture medium in a medium sized cell culture flask (Nunc, Wiesbaden). The next day the DSH-CXL cells were added with fresh medium and cultivated.

The virus containing supernatant of the transfectants was used for transduction of the target cells. The day before transduction the C8166 target cells were transferred to fresh medium in a ratio of 1:2. The supernatants were filter sterilized with a 0.45 μm filter (Sartorius). 7 ml of the supernatant were directly employed for transduction of $2 \times 10^5$ C8166 cells. To stabilize the junction of the retroviral vectors to the cell surface, 40 μg/ml Polybrene were added. Following 2 h of incubation at 37° C. the cells were washed with PBS and transferred into fresh culture medium.

Detection of β-galactosidase activity (X-Gal assay): For examination of a successful transduction an X-Gal assay was carried out after 72 hours according to a modified method of Sanes et al. (1986). The cell culture supernatant was removed and the cells washed with PBS without ($Ca^{2+}$ and $Mg^{2+}$). Subsequently, the cells were overlaid with a fixation solution (2% formaldehyde, 0.2% glutaraldehyde in PBS) for 5 min and washed with PBS. Thereafter, the cells were resuspended in 3 ml of X-Gal reaction mix solution (1 mg/ml, 5 mM K-Ferricyanide, 5 mM K-Ferrocyanide, 2 mM $MgCl_2$). After an approx. 4 h period of incubation of the batch at 37° blue staining of the transduced cells occurred.

6 of the 150 tested scFv-pTC53 expression constructs were cell-specific (M8, K6, 7A5, 7E10, 6C3, 7B4). That means, that per cell-specific construct 10-20 blue-stained C8166 cells could be recognized. Compared to non-cell specific scFv-clones, this result is significant. Stable packaging cell lines were generated from 6 cell-specific scFv expression constructs.

4. Establishment of Stable Packaging Cell Lines.

Preparation of zeocin resistance gene by means of PCR starting from DNA of the plasmid pSCV Zeo (Invitrogen Company): To select packaging cells after a stable transfection with the pTC53-zeo-scFv plasmid for a stable expression of the resistance gene, a zeocin cassette was integrated. For this purpose, a zeocin cassette was amplified by means of recombinant PCR from the vector pZeoSV2 (+/−) of Invitrogen Company (NV Leek, The Netherlands) and provided with the restriction sites NdeI 5' and 3' so that the cassette subsequently could be inserted into the NdeI restricted portion of the pUC19 backbone of pTC53. The PCR-batch (100 μl) contained: 1×PCR buffer (Taq: 10 mM Tris/HCl, pH 8.8, 50 mM KCl, 1.5 mM $MgCl_2$, 0.01% gelatin, 10 μM (+)- and 10 μM (−)-primer, 200 μM of each deoxynucleotide, 2.5 units of Taq polymerase and 100 ng of plasmid DNA. The following oligonucleotides have been used (SEQ ID NOs:34 and 35):

ZEO2184+NDE:
5'-GGAAATTC<u>CATATG</u>GAATTCCCGTTACATAACTTACGGTAAATGGC-3'
         Nde I

ZEO3258-NDE:
5'-GGAATTC<u>CATATG</u>GAATTCCTCAGTCCTGCTCCTCGGCC-3'
       Nde I

The PCR-conditions were: 94° C./3 min, [94° C./1 min, 60° C./1 min, 72° C./1,5 min.] 30 cycles, 72° C./10 min and 4° C. final temperature.

Insertion of a zeocin resistance gene into the scFv pTC53 Env expression constructs positive in the transient test.

Transfection by means of Lipofectamin™ (GIBCO/BRL, Life Technologies, Eggenstein).

Lipofectamin™: N-[2-({2,5bis[-(3-aminopropyl)amino]-1-oxypentyl}amino)ethyl]-N,N-dimethyl-2,3-bis(9-octadecenyloxy)-1-propanaminium trifluoroacetate)/Dioleoylphophatidylethnolamine; 3:1 (w/w)

One day before transfection $1 \times 10^6$ cells were seeded in a 60 mm cell culture dish (Greiner, Nuertingen). For transfection 1-5 µg (depending on the experimental assay) of recombinant plasmid DNA were resuspended in 200 ml serum free medium. Simultaneously 8-25 µl (depending on the experimental assay) Lipofectamin™ were diluted in 200 µl serum-free medium. After combining both solutions a 45 min incubation at room temperature followed. The DNA-liposome mixture was filled up to a final volume of 2 ml and supplied to the cells washed with serumfree medium. Thereafter, the cells were incubated for 5 hours at 37° C. Subsequently, 2 ml of fresh medium containing the double concentration of FCS were added. The next day medium was changed.

For establishing of stable packaging cell clones the cells were overlaid with a selection medium 24 hours after transfection. The Zeocin™ resistance gene (*Streptoalloteichus hinductanus* bleomycin gene) was used as a selection marker. The selection was carried out in DMEM Medium supplemented with 525 µg/ml Zeocin™ (phleomycin from *Streptomyces verticillis*; Invitrogen BV, The Netherlands). The cells were added with fresh selection medium twice a week. After about 4 weeks cell foci representing cell clones could be identified. These colonies were removed individually and transferred into a 24 well plate (flat bottom, Nunc, Wiesbaden) in cell culture medium without antibiotic supplementation. The medium was changed twice a week. When the cells reached a confluence of about 90%, they were expanded into larger cell culture vials.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method for producing cell-specific retroviral vectors, the method comprising
   (a) immunizing a mammal with one or more cell population(s),
   (b) isolating RNA from the immunized mammal, the RNA comprising RNA from a B cell,
   (c) producing, from the isolated RNA, cDNAs that encode single chain antibodies (scFv-cDNAs),
   (d) ligating the scFv-cDNAs into a phagemid vector,
   (e) transforming a host bacterium with the phagemid vector,
   (f) isolating phages that bind to the cell population(s),
   (g) excising the scFv-encoding cDNA from the phages obtained in step (f) and ligating the cDNA into a psi-negative retroviral Env expression vector, comprising an env gene, to produce an Env-scFv expression vector,
   (h) transforming the Env-scFv expression vector into a packaging cell, and
   (i) isolating the retroviral vectors secreted by the packaging cell.

2. The method of claim 1, further comprising isolating cell-specific phages from the phages obtained in step (f), which only bind to the cell population(s) used in step (a), by means of selection.

3. The method of claim 1, wherein step (f) is repeated at least once.

4. The method of claim 1, further comprising the step of:
   (j) isolating the retroviral vectors secreted by the packaging cell, which transduce the cells of the cell population(s), by means of selection.

5. The method of claim 1, wherein the mammal is a mouse, rat, guinea pig, rabbit, goat or sheep.

6. The method of claim 1, wherein the cell population(s) is/are human, mouse, rat, sheep, cattle or pig.

7. The method of claim 1, wherein the cell population(s) is/are T cells, epithelial cells, muscle cells, hematopoietic cells, stem cells, neural cells, carcinoma cells or liver cells.

8. The method of claim 1, wherein the env gene of the psi-negative retroviral Env expression vector is derived from spleen necrosis virus (SNV).

9. The method of claim 8, Wherein the psi-negative retroviral Env expression vector comprises the nucleotide sequence of SEQ ID NO:1.

10. The method of claim 8, wherein the psi-negative retroviral Env expression vector consists of the nucleotide sequence of SEQ ID NO:1.

11. A method for producing cell-specific retroviral vectors, the method comprising:
(a) immunizing a mammal with one or more cell population(s),
(b) isolating RNA from the immunized mammal, the RNA comprising RNA from a B cell,
(c) producing cDNA regions of the variable regions of the immunoglobulin heavy and light chains from the isolated RNA by means of RT-PCR with primers for the immunoglobulin heavy and light chains, wherein the primers comprise the nucleic acid sequence for an oligopeptide linker,
(d) ligating the eDNA regions to scFv-cDNAs,
(e) ligating the scFv-cDNAs into a phagemid vector, and transforming a host bacterium with the phagemid vector,
(f) isolating phages that bind to the cell population(s),
(g) isolating cell-specific phages from the phages obtained in step (f), which only bind to the cell population(s) used in step (a), by means of a selection,
(h) excising the scFv-encoding cDNA from the cell-specific phages obtained in step (g) and ligating the cDNA into a psi-negative retroviral Env expression vector to produce an Env-scFv expression vector,
(i) transforming the resulting Env-scFv expression vector into a packaging cell, and
(j) isolating the retroviral vectors secreted by the packaging cell.

12. A method for producing cell-specific retroviral vectors, the method comprising:
(a) immunizing a mammal with one or more cell population(s),
(b) isolating RNA from the immunized mammal, the RNA comprising RNA from a B cell,
(c) producing cDNA regions of the variable regions of the immunoglobulin heavy and light chains from the isolated RNA by means of RT-PCR with primers for the immunoglobulin heavy and light chains, wherein the primers comprise the nucleic acid sequence for an oligopeptide linker,
(d) ligating the cDNA regions to scFv-cDNAs,
(e) ligating the scFv-cDNAs into a phagemid vector, and transforming a host bacterium with the phagemid vector,
(f) isolating phages that bind to the cell population(s),
(g) isolating cell-specific phages from the phages obtained in step (f), which only bind to the cell population(s) used in step (a), by means of a selection,
(h) excising the scFv-encoding cDNA from the cell-specific phages obtained in step (g) and ligating the cDNA into a psi-negative retroviral Env expression vector comprising the nucleotide sequence of SEQ ID NO:1 to produce an Env-scFv expression vector,
(i) transforming the resulting Env-scFv expression vector into a packaging cell, and
(j) isolating the retroviral vectors secreted by the packaging cell.

* * * * *